US006447525B2

(12) United States Patent
Follmer et al.

(10) Patent No.: US 6,447,525 B2
(45) Date of Patent: *Sep. 10, 2002

(54) APPARATUS AND METHODS FOR REMOVING MATERIAL FROM A BODY LUMEN

(75) Inventors: Brett Follmer, Santa Clara; Stephen Boyd, Moss Beach; Eric Willis, Santa Cruz, all of CA (US)

(73) Assignee: Fox Hollow Technologies, Inc., Redwood City, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/377,894

(22) Filed: Aug. 19, 1999

(51) Int. Cl.⁷ .................................................. A61B 17/22
(52) U.S. Cl. ....................................................... 606/159
(58) Field of Search .................................... 606/159, 110, 606/111, 114, 170, 171, 205, 207

(56) References Cited

U.S. PATENT DOCUMENTS

| | | |
|---|---|---|
| 2,178,790 A | 11/1939 | Henry |
| 3,705,577 A | 12/1972 | Sierra |
| 3,815,604 A | 6/1974 | O'Malley et al. |
| 3,837,345 A | 9/1974 | Matar |
| 3,995,619 A | 12/1976 | Glatzer |
| 4,210,146 A | 7/1980 | Banko |
| 4,696,298 A | 9/1987 | Higgins et al. |
| 4,781,186 A | 11/1988 | Simpson et al. |
| 4,819,635 A | 4/1989 | Shapiro |
| 4,850,957 A | 7/1989 | Summers |
| RE33,258 E | 7/1990 | Onik et al. |
| 4,979,951 A | 12/1990 | Simpson |
| 4,986,807 A * | 1/1991 | Farr .............................. 604/22 |
| 4,994,067 A | 2/1991 | Summers |
| 5,024,651 A * | 6/1991 | Shiber ......................... 606/159 |
| 5,087,265 A | 2/1992 | Summers |
| 5,224,488 A | 7/1993 | Neuffer |

(List continued on next page.)

OTHER PUBLICATIONS

Aug. 19, 1999 (our reference No.: 18489–001000US) entitled *Atherectomy Catheter with Aligned Imager*.

* cited by examiner

Primary Examiner—Kevin T. Truong
Assistant Examiner—Vy Q. Bui
(74) Attorney, Agent, or Firm—Townsend and Townsend and Crew LLP

(57) ABSTRACT

Devices, methods, and kits for removing material from a body lumen. The devices and methods may be used in a variety of body lumens, including but not limited to coronary arteries and other blood vessels. In general, the device or catheter has a scoop-shaped cutting blade mounted on a catheter body for removing material from a body lumen. The cutting blade has a cutting edge that travels a curved path about a pivot point of the blade, preferably moving in an outward direction from the catheter body to engage the target material for removal. The scoop-shaped blade has a collection surface located behind the cutting edge to collect material removed from said body lumen. Advantageously, a scoop-shaped cutting blade according to the present invention facilitates material engagement and the collection surface may be used to bring material back into the catheter body as the blade begins to part-off material. The cutting blade is usually mounted to move in an inward direction towards the catheter body after the cutting edge has engaged the material. The cutting blade can also more easily engage occlusive material that is compressed against the body lumen wall.

28 Claims, 8 Drawing Sheets

U.S. PATENT DOCUMENTS

| | | |
|---|---|---|
| 5,226,910 A | 7/1993 | Kajiyama et al. |
| 5,242,460 A | 9/1993 | Klein et al. |
| 5,250,059 A | 10/1993 | Andreas et al. |
| 5,250,065 A | 10/1993 | Clement et al. |
| 5,285,795 A | 2/1994 | Ryan et al. |
| 5,312,425 A | 5/1994 | Evans et al. |
| 5,318,528 A * | 6/1994 | Heaven et al. ................ 604/95 |
| 5,395,313 A | 3/1995 | Naves et al. |
| 5,431,673 A | 7/1995 | Summers et al. |
| 5,441,510 A * | 8/1995 | Simpson et al. ............ 606/159 |
| 5,505,210 A | 4/1996 | Clement |
| 5,507,292 A | 4/1996 | Jang et al. |
| 5,571,122 A | 11/1996 | Kelly et al. |
| 5,571,130 A | 11/1996 | Simpson et al. |
| 5,584,842 A | 12/1996 | Fogarty et al. |
| 5,620,447 A | 4/1997 | Smith et al. |
| 5,634,464 A | 6/1997 | Jang et al. |
| 5,665,098 A | 9/1997 | Kelly et al. |
| 5,674,232 A | 10/1997 | Halliburton |
| 5,695,506 A | 12/1997 | Pike |
| 5,709,698 A | 1/1998 | Adams et al. |
| 5,733,296 A | 3/1998 | Rogers et al. |
| 5,843,103 A * | 12/1998 | Wulfman .................... 606/159 |
| 6,036,656 A * | 3/2000 | Slater ........................ 600/564 |
| 6,036,707 A * | 3/2000 | Spaulding .................. 606/159 |

# APPARATUS AND METHODS FOR REMOVING MATERIAL FROM A BODY LUMEN

BACKGROUND OF THE INVENTION

The present invention relates generally to apparatus and methods for removing occluding materials from body lumens. More particularly, the present invention relates to the construction and use of atherectomy catheters for excising atheroma and other materials from blood vessels.

Cardiovascular disease frequently arises from the accumulation of atheromatous material on the inner walls of vascular lumens, particularly arterial lumens of the coronary and other vasculature, resulting in a condition known as atherosclerosis. Atherosclerosis occurs naturally as a result of aging, but may also be aggravated by factors such as diet, hypertension, heredity, vascular injury, and the like. Atheromatous and other vascular deposits restrict blood flow and can cause ischemia which, in acute cases, can result in myocardial infarction. Atheromatous deposits can have widely varying properties, with some deposits being relatively soft and others being fibrous and/or calcified. In the latter case, the deposits are frequently referred to as plaque.

Atherosclerosis can be treated in a variety of ways, including drugs, bypass surgery, and a variety of catheter-based approaches which rely on intravascular widening or removal of the atheromatous or other material occluding a blood vessel. Of particular interest to the present invention, a variety of methods for cutting or dislodging material and removing such material from the blood vessel have been proposed, generally being referred to as atherectomy procedures. Atherectomy catheters intended to excise material from the blood vessel lumen generally employ a rotatable and/or axially translatable cutting blade which can be advanced into or past the occlusive material in order to cut and separate such material from the blood vessel lumen. In particular, side-cutting atherectomy catheters generally employ a housing having an aperture on one side, a blade which is rotated or translated by the aperture, and a balloon or other deflecting structure to urge the aperture against the material to be removed.

Although atherectomy catheters have proven to be successful in treating many types of atherosclerosis, known catheter designs may be improved to further enhanced performance. For example, many known side-cutting atherectomy catheters have difficulty in capturing occluding material in the cutting aperture. Conventional atherectomy catheters typically use cutters mounted within openings on the sidewall of the catheter body. Some of these conventional catheters are difficult to position in the body lumen to engage the target tissue or material with these sidewall openings since the catheter must typically be positioned so that material will intrude into the opening. This may make it difficult to remove certain types of obstructions which do not lend themselves to being received in the catheter aperture. Furthermore, catheters which require material to intrude into the catheter aperture limit the aggressiveness with which materials can be removed in severe occlusion type blockages. Additionally, it is often difficult for conventional atherectomy cutters to apply the requisite pressure to cut off the targeted tissue or material. This decreases the effectiveness of these cutters and limits the cutter and catheter designs.

For these reasons, it is desired to provide atherectomy catheters which can access small, tortuous regions of the vasculature and which can remove atheromatous and other occluding materials from within blood vessels in a controlled fashion with minimum risk of injuring the blood vessel wall. In particular, it is desired to provide atherectomy catheters which can facilitate capturing and parting-off of occlusive material. It would also be particularly desirable to have catheters which can remove occlusive material located near the catheter but do not intrude into the catheter aperture. At least some of these objectives will be met by the catheter and method of the present invention described hereinafter and in the claims.

SUMMARY OF THE INVENTION

The present invention provides devices, methods, and kits for removing material from a body lumen. The catheters and methods of the present invention may be used in a variety of body lumens, including but not limited to coronary arteries and other blood vessels. In general, a catheter of the present invention has a scoop-shaped cutting blade mounted on a catheter body for removing material from a body lumen. The cutting blade has a cutting edge that travels a curved path about a pivot point of the blade, preferably moving in an outward direction from the catheter body to engage the target material for removal. The scoop-shaped blade has a collection surface located behind the cutting edge to collect material removed from said body lumen. Advantageously, a scoop-shaped cutting blade according to the present invention facilitates material engagement, and the collection surface may be used to bring material back into the catheter body as the blade begins to part-off material. The cutting blade is usually mounted to move in an inward direction towards the catheter body after the cutting edge has engaged the material. The scoop-shaped cutting blade can also more easily engage occlusive material that is compressed against the body lumen wall since the blade may be mounted to extend outward from the catheter body.

Desirably, the blade or blades of the catheter will be actuable with the application of reasonable mechanical forces which are capable of being transmitted along even rather lengthy catheters. Further desirably, the catheters will be suitable for directional removal of occluding material and will include mechanisms for engaging cutting blades against selected portions of a vascular wall. Optionally, the catheter should permit blood perfusion during performance of an atherectomy procedure. Preferably, but not necessarily, the cutting edge of the cutting blade will extend outside of the catheter body to engage material in a body lumen. Typically, the cutting blade rotates to place the cutting edge in the desired position. The arc defined by the rotation of the cutting blade is usually large enough to place the cutting edge outside the boundaries of the catheter body. The aperture from which the cutting blade extends may be located at a variety of positions on the catheter body, such as along the sidewall of the catheter or at the distal end of the catheter body. Devices having the cutting blade located at the distal end of the catheter may be used to bore through material in a substantially occluded body lumen. Preferably, the cutting blade has a mating surface on the catheter body to assist in the parting-off or cutting of material.

According to the present invention, embodiments of the catheter may have a scoop-shaped cutting blade that reciprocates longitudinally along a guide, such as a slotted track, a rail, or a ramp, to a position outside the catheter body. Furthermore, the cutting blade may be rotated about its pivot point while the blade is reciprocated longitudinally. A cutting blade that travels longitudinally while rotating about its pivot point can simulate the movement of a surgical curette/bone scraping device to remove greater amounts of material from the body lumen. Advantageously, such a rotating and translating motion may allow the catheter to lie stationary in the body lumen while the cutting blade travels out from the catheter body to grab material and return towards the catheter body to part it off. Rotation and translation also allows material to be removed and collected in a simultaneous manner. Rotation of the cutting blade may also increase the amount of force that may be applied against the material (since both translational and rotational force may be applied). The cutting blades used on the present invention may also include needles or other sharpened points to penetrate into the material to grasp the material before it is parted off.

In another aspect of the present invention, a method is provided for excising occlusive material from within a body lumen. The method comprises positioning a catheter body having a scoop-shaped cutting blade adjacent to a target material in the body lumen. Material may be parted off from the body lumen by rotating the cutting blade about a pivot point to engage and cut the target material while urging the material into the catheter body with a material collection surface on the cutting blade. Of course, in some embodiments, the cutting blade may translate longitudinally while being rotated about a pivot point of the cutting blade. The longitudinal moving step usually involves reciprocating the cutting blade between a first position where the cutting edge is outside the catheter body and a second position where the cutting edge is substantially within the catheter body.

In a still further aspect, kits according to the present invention will comprise a catheter having a material capture device. The kits will further include instructions for use setting forth a method as described above. Optionally, the kits will further include packaging suitable for containing the catheter and the instructions for use. Exemplary containers include pouches, trays, boxes, tubes, and the like. The instructions for use may be provided on a separate sheet of paper or other medium. Optionally, the instructions may be printed in whole or in part on the packaging. Usually, at least the catheter will be provided in a sterilized condition. Other kit components, such as a guidewire, may also be included.

A further understanding of the nature and advantages of the invention will become apparent by reference to the remaining portions of the specification and drawings.

DESCRIPTION OF THE SPECIFIC EMBODIMENTS

Figure 1:
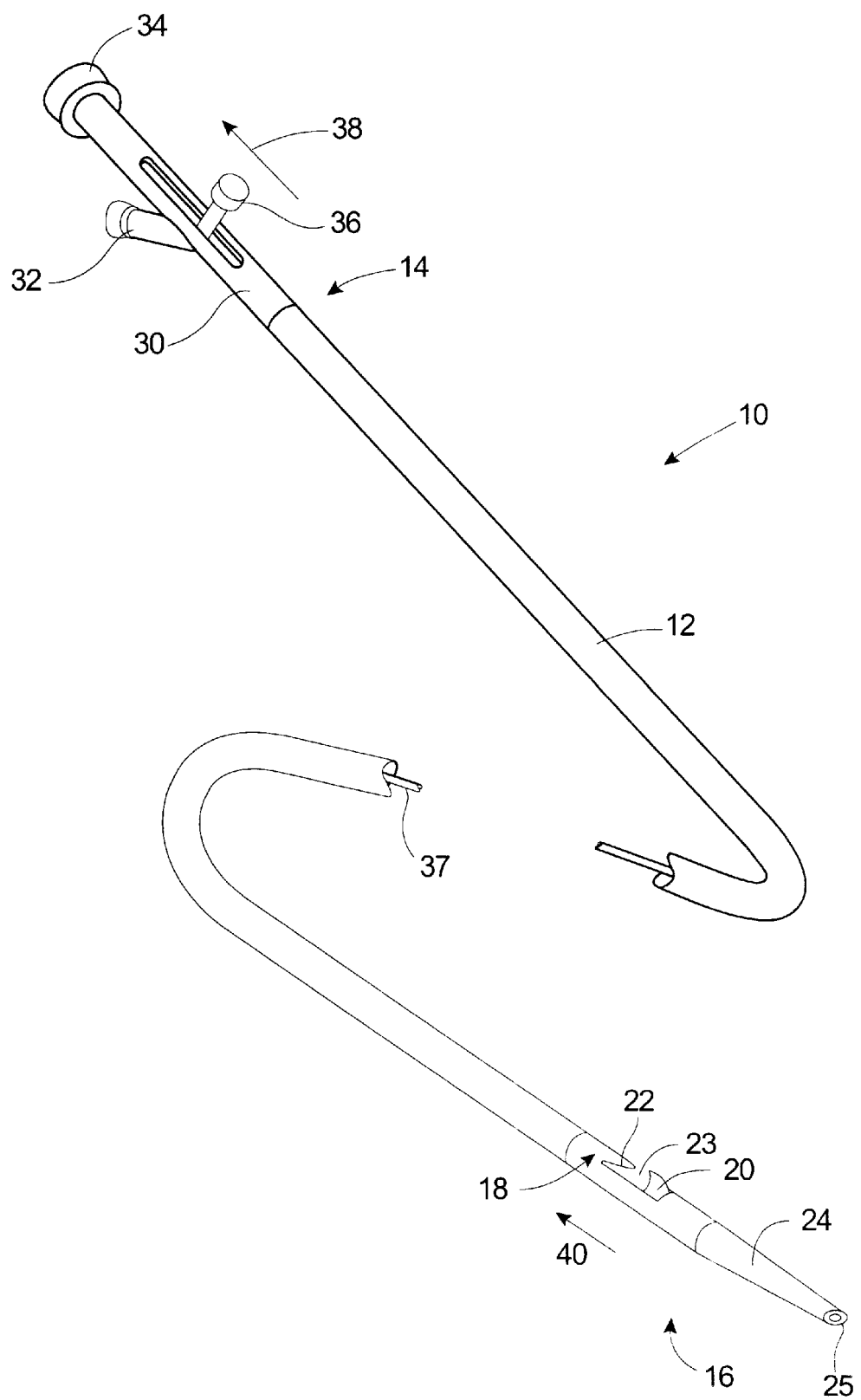
FIG. 1 is a perspective view of an atherectomy catheter constructed in accordance with the principles of the present invention.

The present invention provides devices, methods, and kits for use in removing material from a body lumen. The present invention may be used in a variety of body lumens, including but not limited to coronary and other arteries. Advantageously, the present invention facilitates the engagement and removal of materials in the body lumen. The invention may also be adapted to remove larger amounts of material in each cutting motion.

Apparatus according to the present invention will comprise catheters having catheter bodies adapted for intraluminal introduction to the target body lumen. The dimensions and other physical characteristics of the catheter bodies will vary significantly depending on the body lumen which is to be accessed. In the exemplary case of atherectomy catheters intended for intravascular introduction, the catheter bodies will typically be very flexible and suitable for introduction over a guidewire to a target site within the vasculature. In particular, catheters can be intended for "over-the-wire" introduction when a guidewire lumen extends fully through the catheter body or for "rapid exchange" introduction where the guidewire lumen extends only through a distal portion of the catheter body.

Catheter bodies intended for intravascular introduction will typically have a length in the range from 50 cm to 200 cm and an outer diameter in the range from 1 French (0.33 mm; Fr.) to 12 Fr., usually from 3 Fr. to 9 Fr. In the case of coronary catheters, the length is typically in the range from 125 to 200 cm, the diameter is preferably below 8 Fr., more preferably below 7 Fr., and most preferably in the range from 2 Fr. to 7 Fr. Catheter bodies will typically be composed of an organic polymer which is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, axial filaments, or the like, in order to increase rotational strength, column strength, toughness, pushability, and the like. Suitable catheter bodies may be formed by extrusion, with one or more lumens being provided when desired. The catheter diameter can be modified by heat expansion and shrinkage using conventional techniques. The resulting catheters will thus be suitable for introduction to the vascular system, often the coronary arteries, by conventional techniques.

The cutting blades used in the present invention will usually be formed from a metal, but could also be formed from hard plastics, ceramics, or composites of two or more materials, which can be honed or otherwise formed into the desired cutting edge. In the exemplary embodiments, the cutting blades are formed as coaxial tubular blades with the cutting edges defined in aligned apertures therein. It will be appreciated that the present invention is not limited to such preferred cutting blade assemblies, in a variety of other designs, such as the use of wiper blades, scissor blades or the like. Optionally, the cutting edge of either or both the blades may be hardened, e.g., by chrome plating. A preferred chrome plating material is ME-92, available from ME-92 Operations, Inc., which may be applied according to manufacturer's instructions. Of course, other precision thin-film hard coatings such as a titanium nitride layer from Bry-Coat™ may be used to engineer the desired surface properties.

Referring now to FIG. 1, a catheter 10 constructed in accordance with the principles of the present invention comprises a catheter body 12 having a proximal end 14 and a distal end 16. The catheter body 12 typically includes a cutting mechanism 18 integrally formed with and considered part of the catheter body. The cutting mechanism 18 may of course be a separate part which is attached to the distal end of the catheter body during manufacture. The cutting mechanism 18 comprises a first cutter 20 and a second cutter 22 that provides a mating surface against which material may be parted off. The first cutter 20 may be a scoop-shaped cutting blade that cuts material that is near the vicinity of the aperture 23. An atraumatic tip 24 is attached to the distal end of the catheter body, and a guidewire lumen 25 extends through the entire catheter body, cutting mechanism 18, and terminates in port 25 at the distal tip of tip section 24. A proximal hub 30 is attached to the proximal end of catheter body 12 and comprises a perfusion/aspiration connector 32, a guidewire connector 34, and a slider 36. The slider 36 is attached to the proximal end of an actuator rod 37 which extends from the hub 30 through the lumen of catheter body 12 into the cutting mechanism 18 where it is attached at a proximal end of the first cutter 20. In this way, manual actuation of slider 36 in the direction of arrow 38 moves first cutter 20 in the direction of arrow 40.

Figure 2:
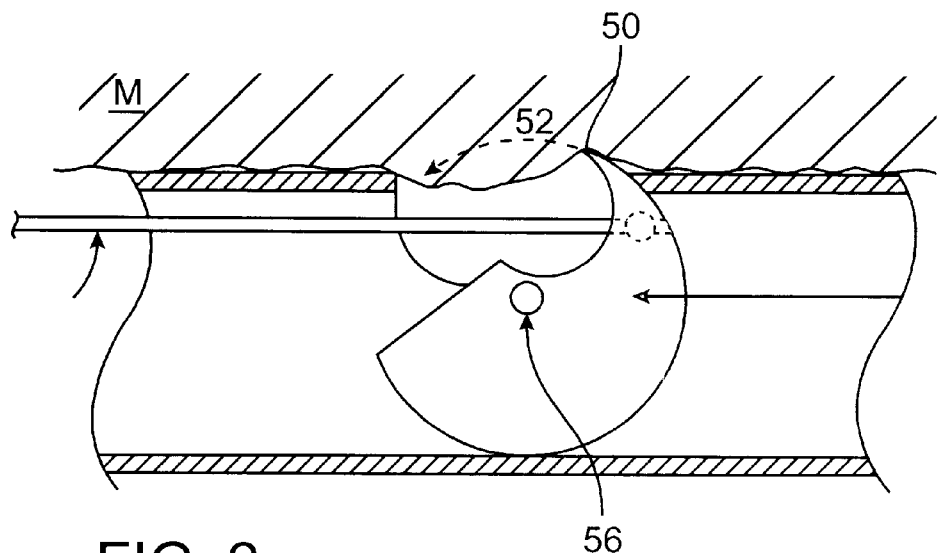
FIGS. 2–4 show cross-sectional views of a cutting blade according to the present invention mounted in the catheter of FIG. 1.
Figure 3:
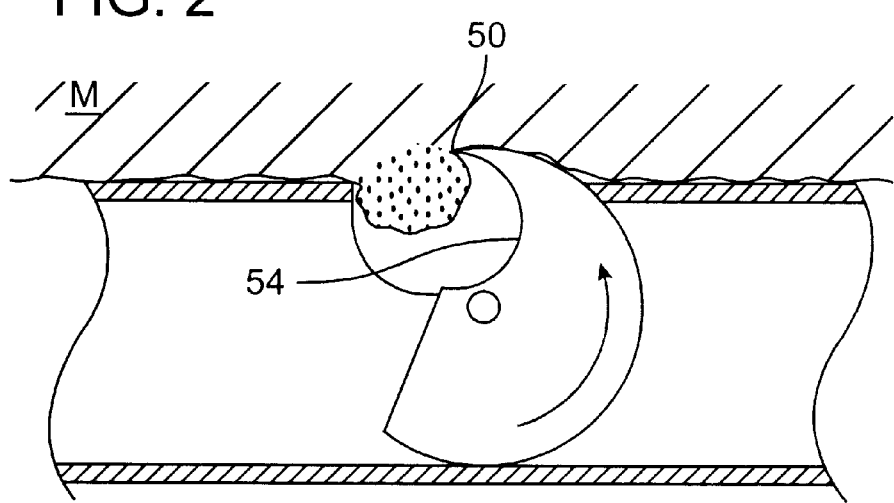
Figure 4:
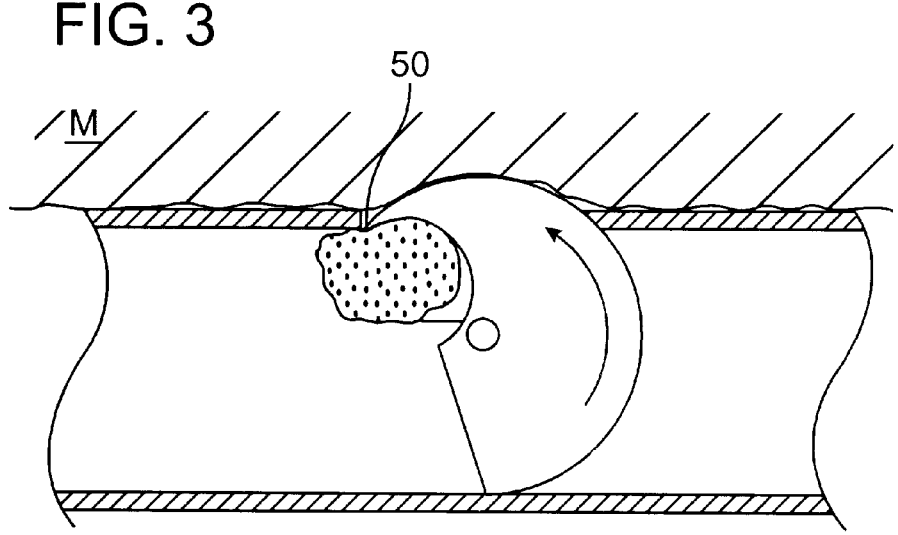

Referring now to FIGS. 2–4, the cutting motion of blade 20 will be described in detail. In this embodiment of the cutting mechanism 18, the first cutter or cutting blade 20 is a scoop-shaped cutting blade as seen in FIG. 2. As the blade 20 rotates through its range of motion, the cutting edge 50 of the blade will draw an arc (as indicated by the dotted line 52) that extends outward from the aperture 23 for a portion of the blade's path. As seen in FIG. 3, this allows the blade 20 to engage material that has intruded into the aperture 23 or to move outside the diameter of the catheter to engage those materials in the outward vicinity of the aperture 23. Some cutting may occur along the cutting edge 50 as the first blade 20 engages the material M. The parting-off of the material is usually completed when the cutting edge 50 clears, or in some cases engages, the mating surface or edge of the second cutter 22 as shown in FIG. 4.

A material collection surface 54 is usually located behind the cutting edge 50 on the cutting blade 20 in the direction of cutting. The collection surface 54, as shown in FIGS. 3 and 4, will urge material M towards the interior of the catheter. The collection surface 54 may be concave or cupped surface which can more easily contain the material M that is to be parted off. The scoop-shaped cutting blade 20 may assume various shapes similar to a spoon, a bowl, a shovel blade, a claw, or the like. The curved shape of the cutting blade 20 allows the blade to be substantially contained within the catheter during delivery but extend outside the boundaries of the catheter body to engage material during cutting.

The first blade 20 may be actuated in various manners. As shown in the sequence of FIGS. 2–4, a pullwire 55 is used to rotate the cutting blade 20 about a pivot point 56. The pivot point 56 may be defined by a pin passing through the blade 20 or by a protrusion on the blade which sits in a recess on the body portion of the cutting mechanism. Spring mechanisms, gears, or various cable-based systems of reduced size may also be used to rotate the cutting blade 20.

Figure 6:
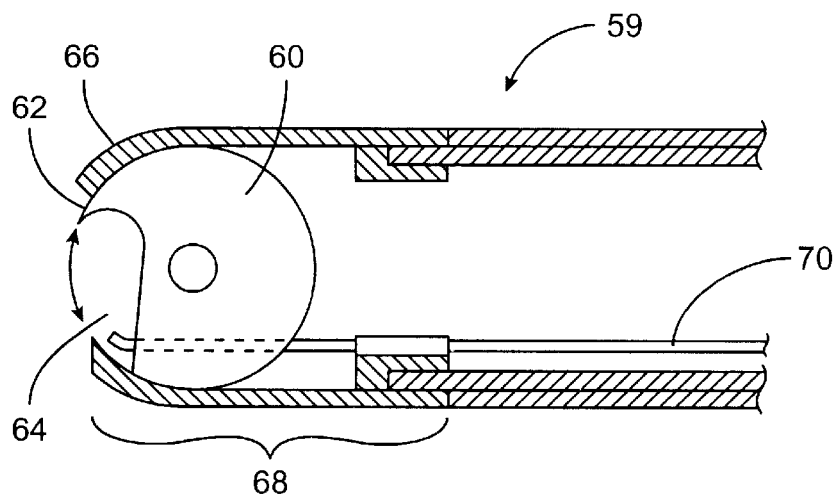
FIGS. 5–8 show various views a cutting blade according to the present invention mounted at the distal end of the catheter.
Figure 5:
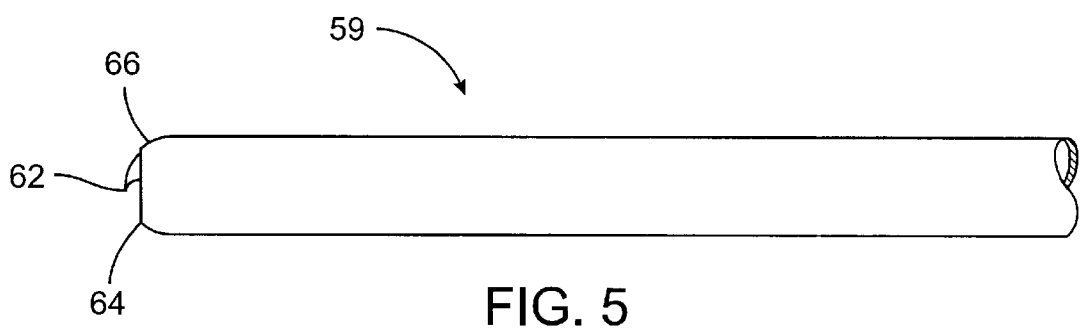

Referring now to FIGS. 5–8, catheters having cutting blades located at the distal end of the catheter body will now be described. FIGS. 5 and 6 show catheter 59 having a spherical or "scoop-shaped" cutting blade 60 with a cutting edge 62 that can extend outwardly from an aperture 64 located at the distal end of the catheter. Positioning the cutting blade 60 in this manner allows the catheter to bore through obstructions in the body lumen. The cutting edge 62 can travel outward towards obstructive material to engage and then part-off the material. The distal end 66 of the catheter around the aperture 64 may be swaged to conform to the curved contours of the cutting blade. This creates an atraumatic outer surface that would advantageously allow the catheter to remove material from the center of a tubular body lumen without damaging the wall of the tubular member. The cutting zone in this embodiment would be spaced apart from the walls of the tubular body lumen or member. Advantageously, such a swaged distal end would enable the device to bore into a stenosis within a stent and not contact the stent struts. Such a device, along with the embodiment shown in FIGS. 1–5, creates a device having a reduced rigid length since the rotating scoop-shaped cutter 20 and 60 rely on rotational instead of translational motion. As seen in FIG. 6, the rigid length is denoted by bracket 68. Like the device of FIGS. 2–4, a pullwire 70 is used to rotate the cutting blade 60.

Figure 7:
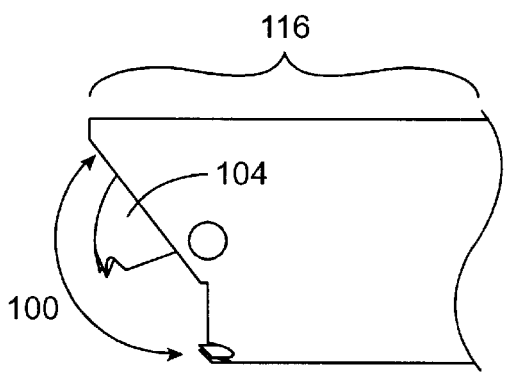
Figure 8:
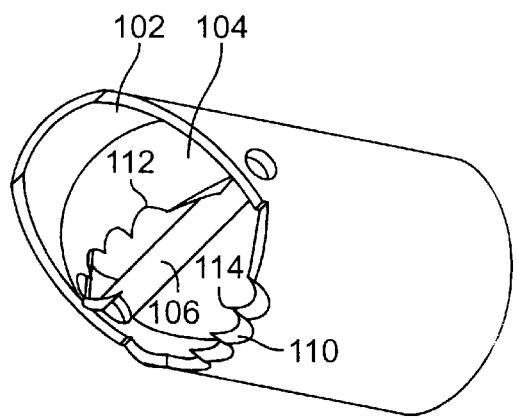

The positioning and exposure of the cutting blade on the distal end of the catheter may be varied. FIGS. 7 and 8 show that the aperture 100 and the distal end 102 of the catheter may be shaped to facilitate material removal in a certain direction or for more aggressive material removal. The aperture 100 in FIGS. 7 and 8 allows for more radial motion of the cutting blade than the aperture 64 in the device of FIG. 5. The aperture 100 may allow the device to remove larger amounts of material with each cutting motion when more aggressive removal is desired. As seen in FIG. 8, the cutting blade 104 uses a pivot pin or bar 106 to mount the cutting blade to the distal end 102. The cutting blade 104 works in conjunction with a second cutting edge 110 which mates with the cutting edge 112 on the cutting blade. Preferably, the cutting edges 110 and 112 have teeth or penetrating point 114 which can penetrate the material and allow the cutter to grasp the material and draw it inwards towards the interior of the catheter. Again, it can be seen that the cutting mechanism has a reduced rigid length 116 (FIG. 7) allowing the catheter to navigate body lumens with tortuous configurations.

Figure 9:
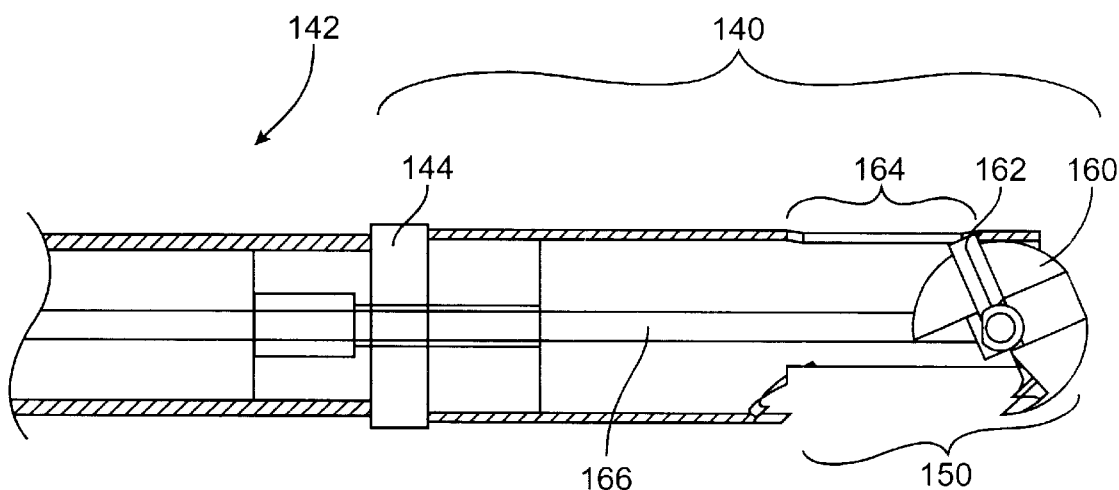
FIGS. 9–10 are cross-sectional views of a cutting blade which may rotate and translate longitudinally along the catheter.
Figure 10:
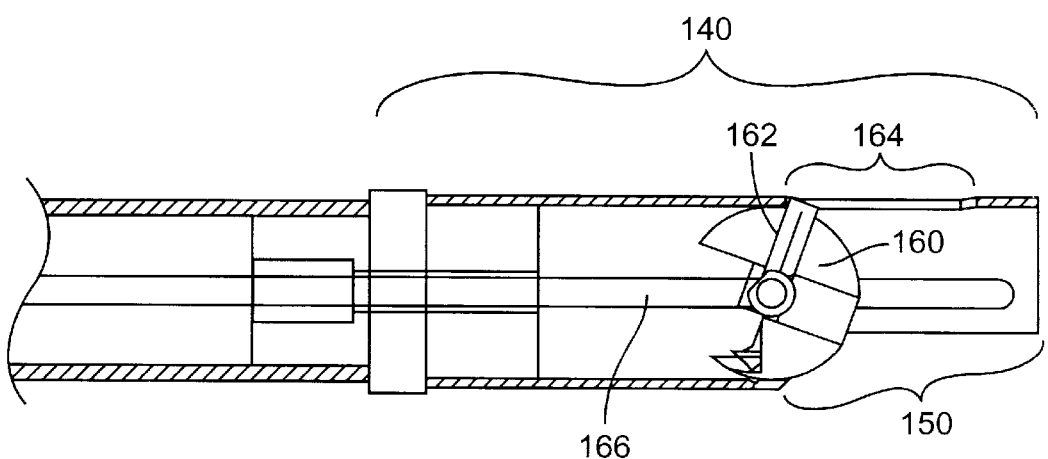

In another aspect of the present invention, the spherical or scoop-shaped cutting blades according to the present invention may be designed for both translational and rotational motion. Referring now to FIGS. 9 and 10, one embodiment of a catheter with such a cutting mechanism will be described. FIG. 9 shows a cutting mechanism 140 mounted on a catheter 142 via a shaft adaptor 144. The cutting mechanism 140 has a distal aperture 150 that opens along the side wall of the mechanism and extends to the forward facing distal end of the mechanism. A cutting blade 160 is mounted to reciprocate axially within the aperture 150. The cutting blade 160 has a stem 162 that slides within a slot 164 along the wall of the cutting mechanism 140. The stem 162 places limits on the motion of the cutting blade 160 to create rotational movement of the cutting blade 160 at the distal-most and proximal-most positions. FIG. 9 shows the blade 160 at a distal-most position while FIG. 10 shows the cutting blade at a proximal-most position. When the center extension rod 166 pushes the cutting blade 160 past the distal limit of the slot 164, the cutting blade rotates forward. When the extension rod 166 pulls the cutting blade 160 past the proximal limit of slot 164, the cutting blade rotates backwards to complete the cutting motion. Moving the cutting blade 160 longitudinally along the cutting mechanism increases the amount of material that can parted off in each stroke of the cutting blade. As the blade 160 extends outside the aperture 150 when positioned for cutting, it may also engage material more easily.

Figure 11:
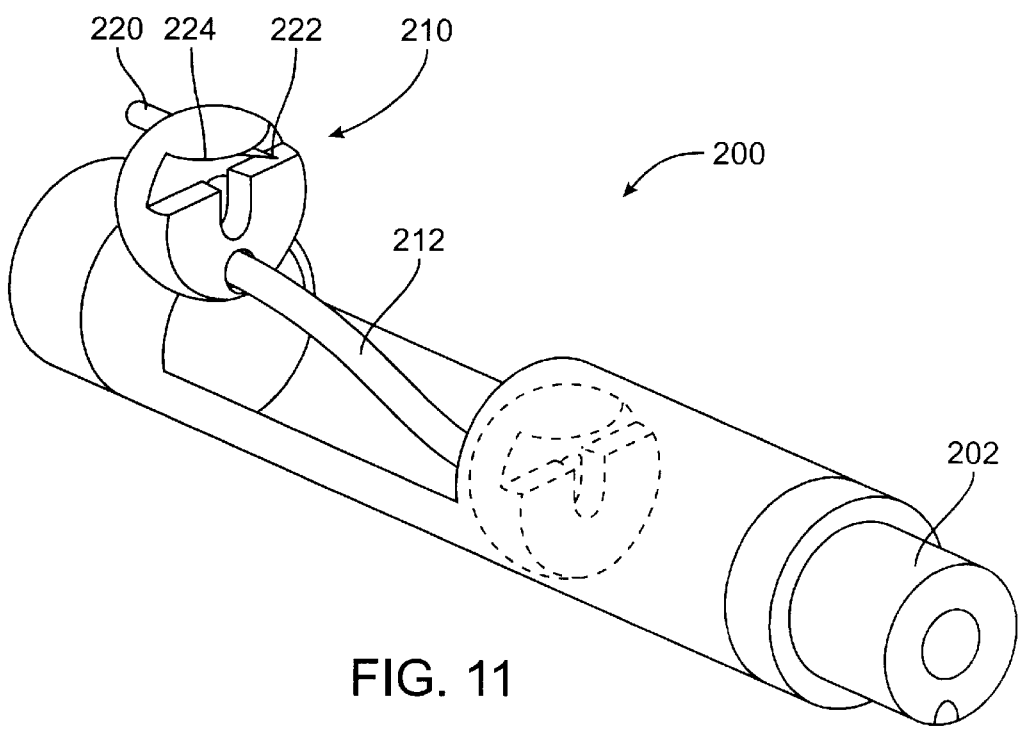
FIGS. 11–13 depict further embodiments of a cutting blade according to the present invention which move along a longitudinal path.
Figure 12:
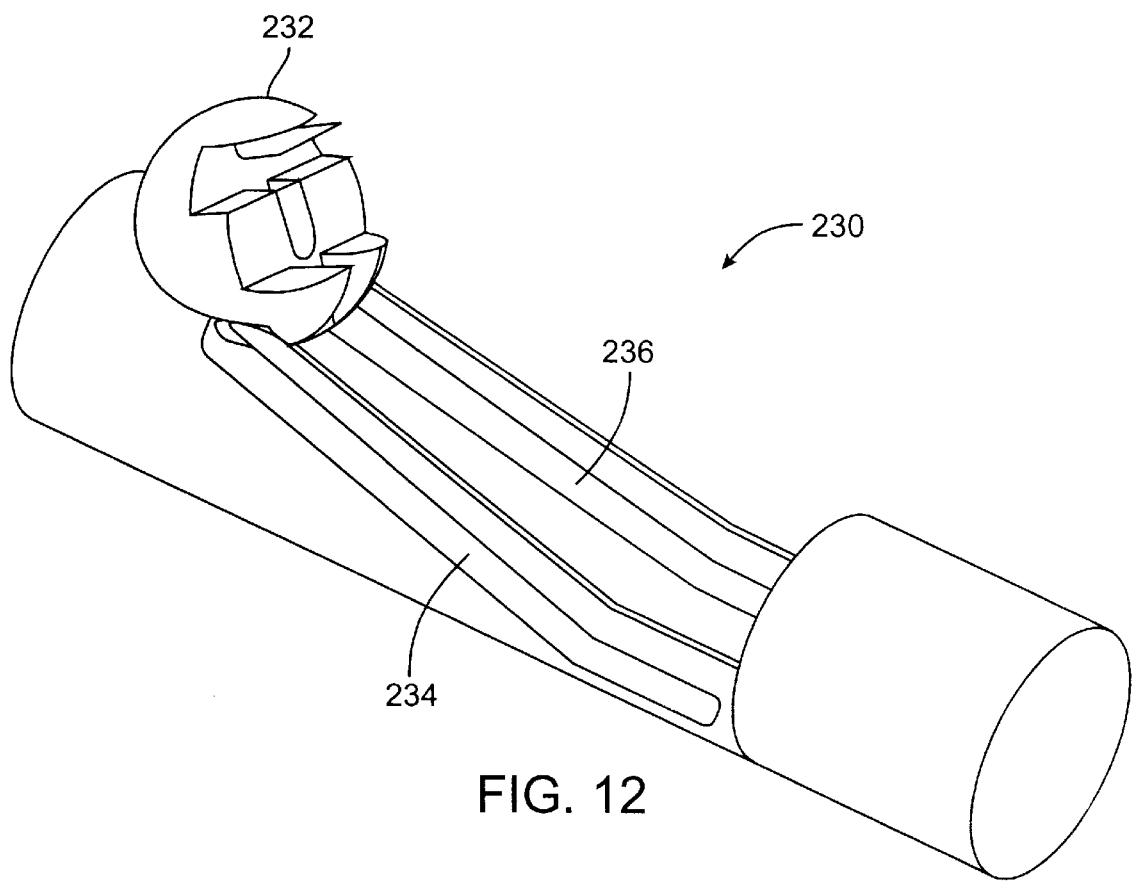

Referring now to FIGS. 11–12, another catheter-mountable cutting mechanism having a longitudinally reciprocating cutting blade will be described. FIG. 11 shows a cutting mechanism 200 with a shaft adaptor 202 for coupling with a catheter body. The mechanism 200 has a ball-shaped cutting blade 210 mounted on a rail 212 that guides the cutting blade between a first position outside the diameter of the cutting mechanism (FIG. 11) and a second position substantially within the cutting mechanism (shown in phantom). By having a cutting blade 210 travel on a rail and move outside the profile of the cutting mechanism 200 as shown in FIG. 11, the catheter and cutting mechanism can advantageously lie stationary while the blade travels outside the mechanism to capture and part-off material. The cutting blade 210 as shown in FIG. 11 is mounted with at least one needle 220 for penetrating material. The sharpened end 222 of the needle 220 is preferably located in front of the cutting edge 224 so that the needle can help the cutting blade 210 engage the material. The blade 210 may be designed to have a plurality of material penetrating members.

Figure 13:
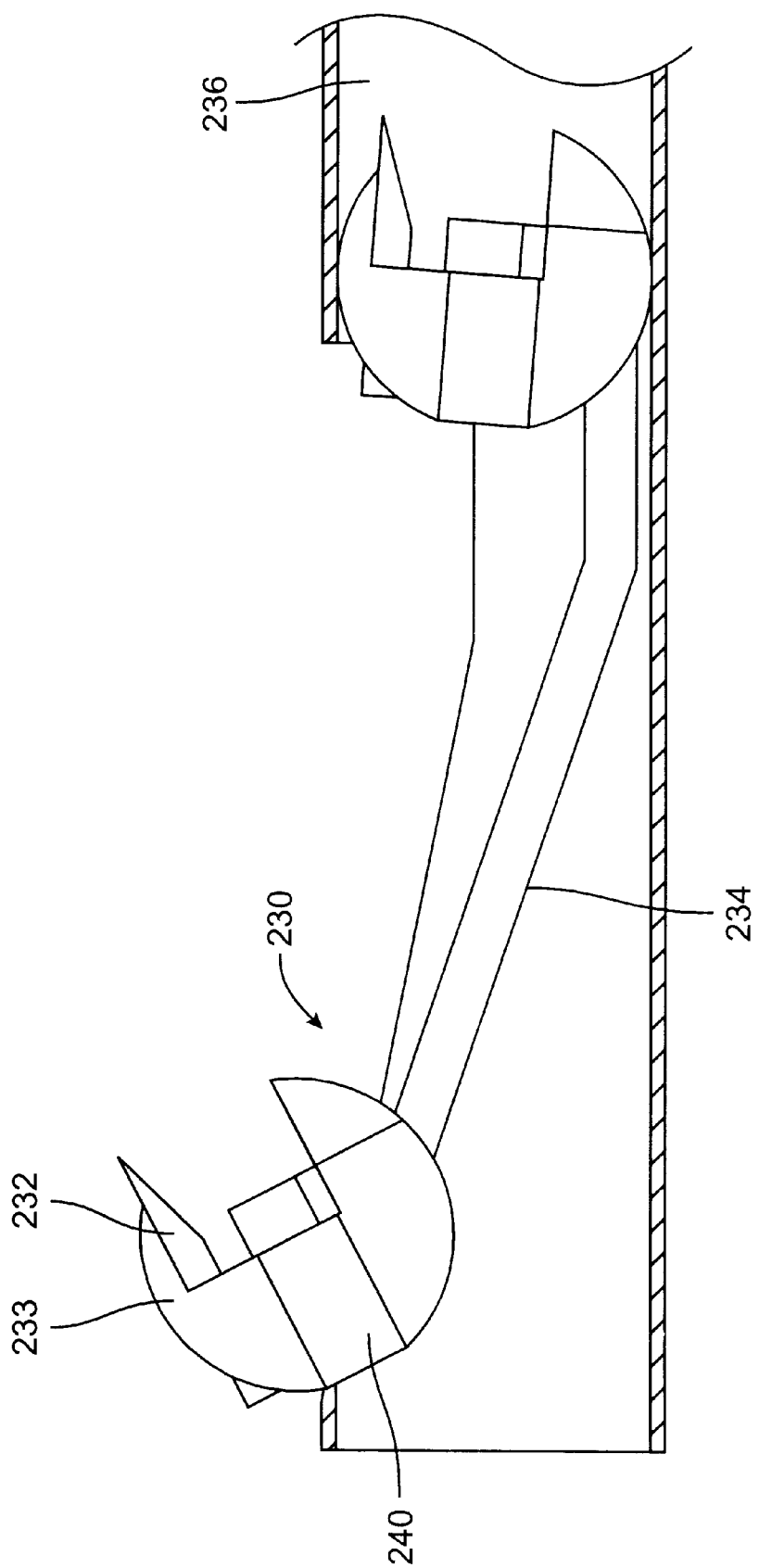

Referring now to FIGS. 12 and 13, another cutting mechanism with a longitudinally moving cutting blade will now be described. FIG. 11 shows a cutting mechanism 230 with a cutting blade 232 mounted in a ball or scoop 233 that reciprocates along cutter tracks 234 formed in a housing 236. Like the device shown in FIG. 11, the cutting blade 232 travels outside the diameter of the cutting housing 236 to engage material in the body lumen. As seen in FIG. 13, the cutting blade 232 may be mounted with a stem 240 to cause rotation of the cutting blade when it is moved to the outermost position along the cutter track 234. The cutting blade 232 may be actuated by various methods such as by pullwires, or the like. For example, the cutting blade may be actuated by either a central or off-center pullwire where the slot acts as a travel limit to cause rotation of the cutting blade at the end of the blade's travel.

Figure 14:
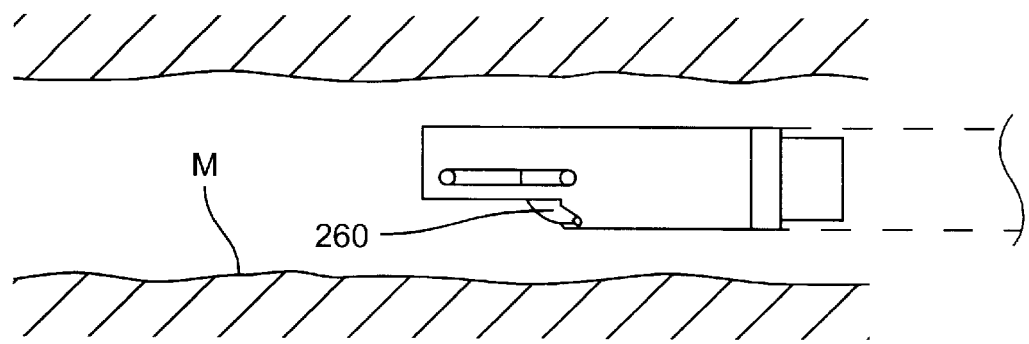
FIGS. 14–17 show a cutting blade of FIG. 9 used to remove material from a body lumen.
Figure 15:
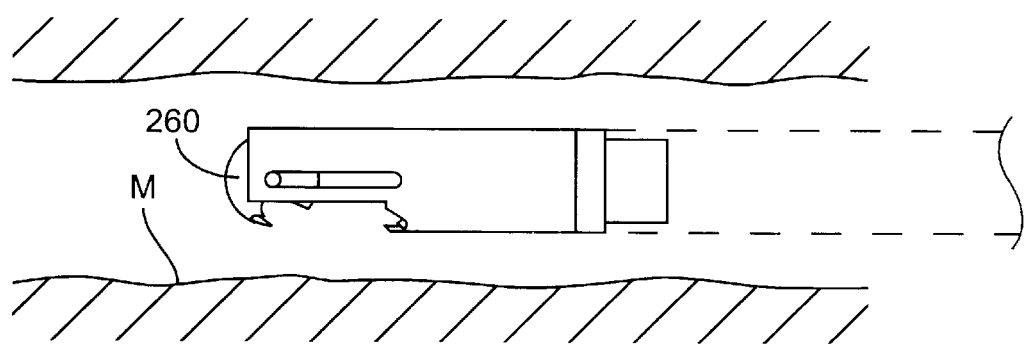
Figure 16:
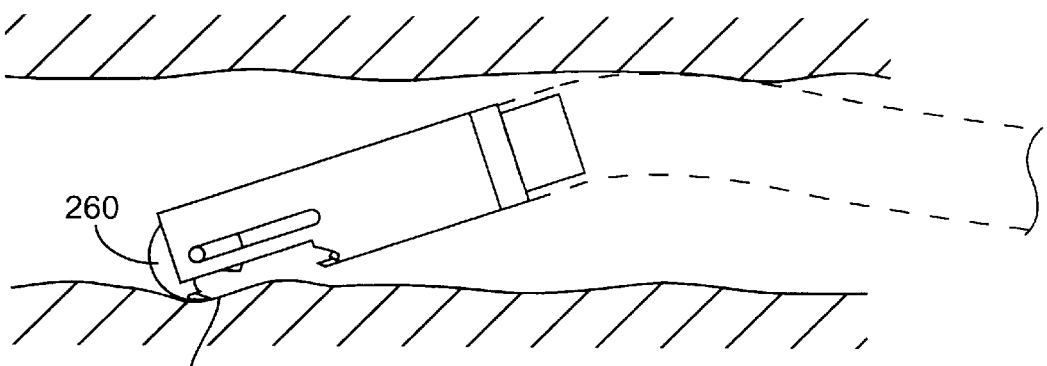
Figure 17:
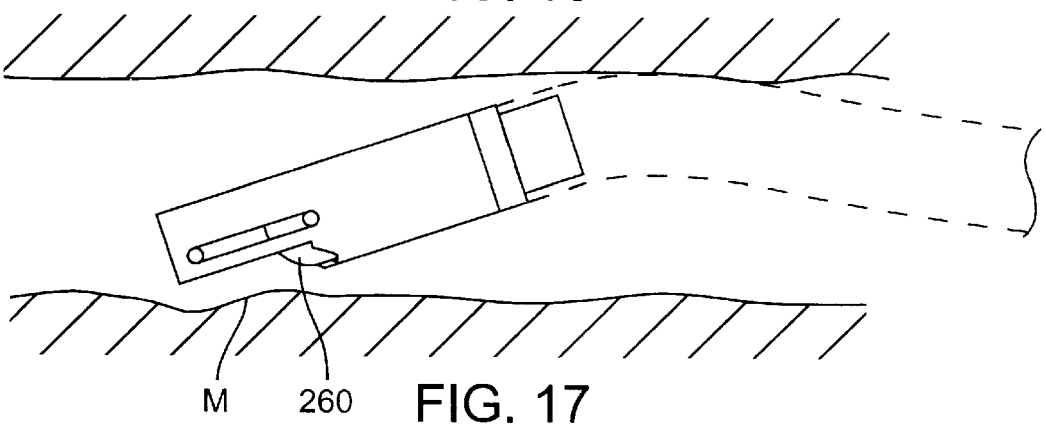

Referring now to FIGS. 14–17, the cutting motion of a translational and rotational cutting blade as shown in FIG. 9 will be further described. The cutting blade 260 on the cutting mechanism in FIG. 14 may be mounted with an articulating or steerable catheter (shown in phantom) to position the cutting blade as desired. This allows the cutting blade 260 to be more easily positioned against material in the body lumen and also adjust the direction of material removal. As seen in FIG. 14, the cutting blade 260 is usually delivered with the cutting blade in a closed or retracted position. When the cutting mechanism nears the target material M, the cutting blade is moved to the open position as seen in FIG. 15. When a steerable or articulating catheter is used, the cutting mechanism can be angled (FIG. 16) to more aggressively remove material from the body lumen. The cutting blade 260 will retract and rotate to part-off the body lumen material (FIG. 17). The cutting blade 260 may rotate about its pivot point while it is being retracted or at the end of the retraction. Where the cutting mechanism is mounted on a nonsteerable catheter, the cutting mechanism may lie substantially parallel against the body lumen wall, and the cutting blade 260 will move longitudinally to scrape material from the body lumen wall.

Figure 18:
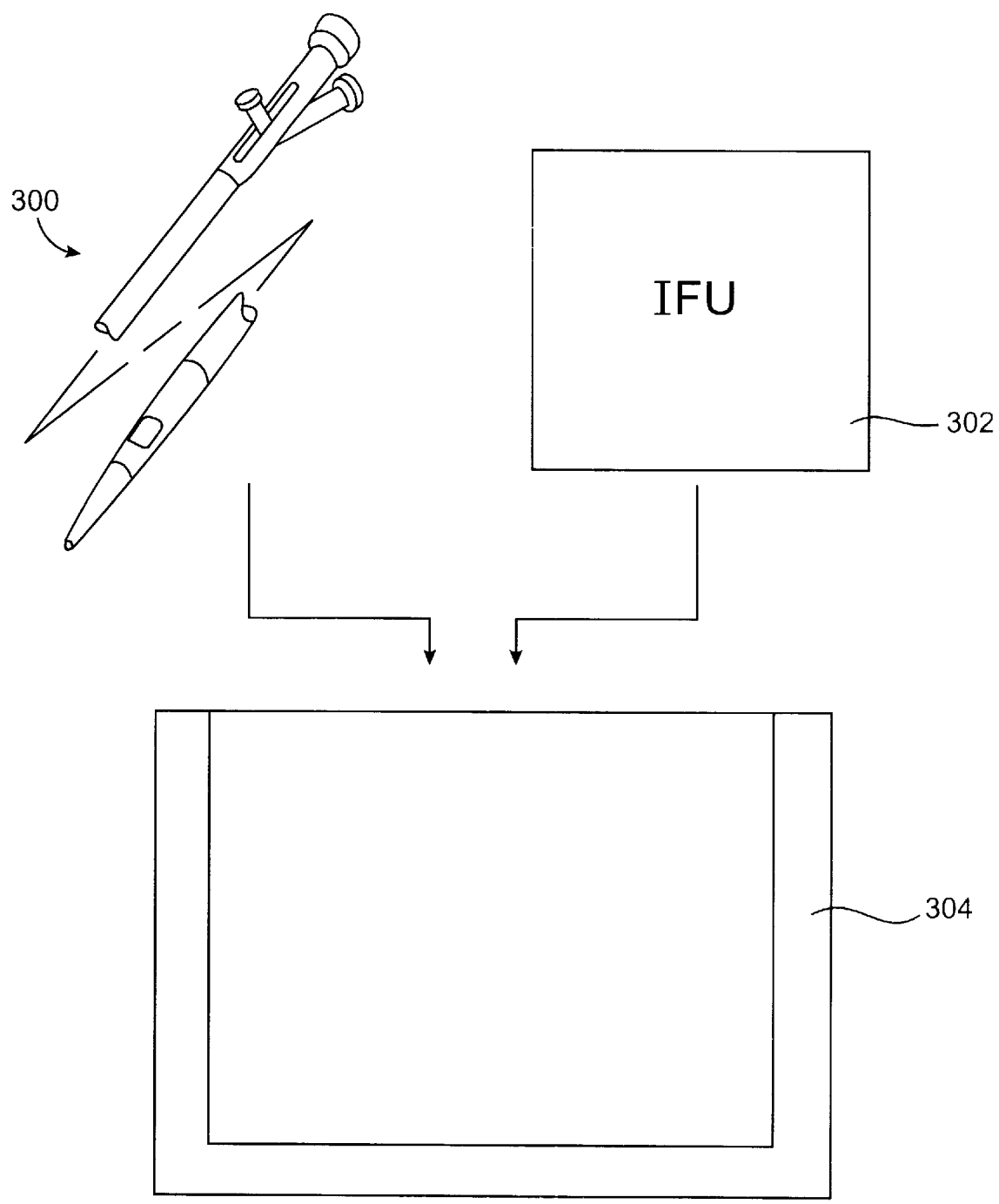
FIG. 18 shows a kit according to the present invention.

Referring now to FIG. 18, the present invention will further comprise kits including catheters 300, instructions for use 302, and packages 304. Catheters 300 will generally be as described above, and the instruction for use (IFU) 302 will set forth any of the methods described above. Package 304 may be any conventional medical device packaging, including pouches, trays, boxes, tubes, or the like. The instructions for use 302 will usually be printed on a separate piece of paper, but may also be printed in whole or in part on a portion of the packaging 304.

While all the above is a complete description of the preferred embodiments of the inventions, various alternatives, modifications, and equivalents may be used. For example, the cutting blade may be oriented to cut along a variety of angles relative to the longitudinal axis of the catheter body. The cutting blade may be adapted for use with a tissue or material capture device which is located in front of and sometimes spaced apart from the cutting blade. A suitable capture device is described further in commonly assigned, copending U.S. application Ser. No. 09/377,884 (Attorney Docket No. 18489-001600US) filed on the same day as the present application, the full disclosure of which is incorporated herein by reference. In some embodiments, the scoop-shaped blade may appear similar to a claw or a shovel. The term "scoop-shaped" as used herein refers generally to a device that has a cutting edge and a collection surface. Typically, the collection surface is a concave surface located behind the cutting edge in the cutting direction. In some alternative embodiments, the scoop-shaped cutting blade may have adjacent perpendicular walls to form the collection surface. Although the foregoing invention has been described in detail for purposes of clarity of understanding, it will be obvious that certain modifications may be practiced within the scope of the appended claims.

What is claimed is:

1. A catheter for removing material from a wall of a body lumen, said catheter comprising:
   a catheter body having a proximal end, a distal end, and a side opening cutting window wherein said catheter body defining an outer diameter; and
   a rotatable cutting blade coupled to an actuator through a flexible elongated drive shaft and movably disposed in said catheter body to reciprocate along a longitudinal path within said cutting window, said cutting blade having a cutting edge and a material collection surface;
   wherein said cutting blade is configured to travel along a curved path outside of the side opening cutting window and beyond the outer diameter of said catheter body, wherein said material collection surface is located adjacent said cutting edge to collect material removed from said body lumen towards the cutting window.

2. A catheter as in claim 1 wherein said cutting edge is configured to move along a portion of said curved path in an outward direction from the catheter body to engage material that does not extend through said side cutting window.

3. A catheter as in claim 1 wherein said cutting edge of the cutting blade is mounted to move in an inward direction towards said catheter body after said cutting edge has engaged said material.

4. A catheter as in claim 1 wherein said material collection surface comprises a concave surface.

5. A catheter as in claim 1 wherein said cutting blade includes at least one penetrating point mounted on said cutting blade to engage said material before said cutting edge contacts said material.

6. A catheter as in claim 1 wherein said drive shaft comprises a pullwire coupled to said cutting blade.

7. A catheter as in claim 1 wherein said catheter body has a shaft adaptor at said proximal end.

8. A catheter as in claim 1 wherein said catheter body comprises a cutting mechanism, said cutting blade coupled to said cutting mechanism.

9. A catheter for removing material from a body lumen, said catheter comprising:
   a catheter body having a proximal end, a distal end, and a side opening cutting window; and a scoop-shaped cutting blade mounted on the catheter body and coupled to an actuator, said cutting blade having a cutting edge and a material collection surface;

wherein said cutting is configured to travel along a curved path about a pivot point of said cutting blade and wherein said material collection surface is located behind said cutting edge to urge material removed from said body lumen towards the catheter body;

wherein said cutting blade is mounted on said catheter body to reciprocate along a longitudinal path on said catheter body, wherein said cutting blade uses a guide for defining said longitudinal path, said guide selected from the group consisting of a slotted track, a rail, or a ramp on said catheter body;

wherein said cutting blade is mounted on said catheter body to rotate about an axis perpendicular to a longitudinal axis of said catheter body.

10. A catheter as in claim 9 wherein said cutting blade is mounted to reciprocate along said longitudinal path between a first position placing said cutting edge outside of said catheter body and a second position placing said cutting edge substantially within said catheter body.

11. A catheter as in claim 9 wherein said cutting blade includes a material engaging member mounted on said cutting blade to engage said material before said cutting edge contacts said material.

12. A catheter for removing material from a body lumen, said catheter comprising:

a catheter body having a proximal end, a distal end, and a side opening cutting window, wherein said catheter body defining an outer diameter; and a cutting blade having a concave surface coupled to an actuator through a drive shaft, wherein the material contacting portion of the cutting blade is movable along the longitudinal path within the catheter body and movable outside the side opening cutting window and beyond the outer diameter of said catheter body so as to remove the material from the body lumen.

13. The catheter of claim 12 wherein the cutting blade is rotatable.

14. The catheter of claim 6 wherein proximal movement of the cutting blade removes material from the body lumen.

15. The catheter of claim 13 wherein the cutting blade moves outside of the cutting window to engage material that does not substantially extend through the cutting window.

16. The catheter of claim 15 wherein the cutting blade is moved through tensioning of the drive shaft.

17. The catheter of claim 12 wherein the cutting blade draws the severed material into a collection chamber in the catheter body.

18. A catheter for removing material from a body lumen, said catheter comprising:

a catheter body having a proximal end, a distal end, a side opening cutting window wherein said catheter body defining an outer diameter, and defining a longitudinal axis; and an axially movable rotating cutting blade having a concave surface coupled to an actuator through a drive shaft, wherein the material contacting portion of said cutting blade is movable between a first position placing said cutting edge beyond the outer diameter of said catheter body and the side opening cutting window and a second position placing said cutting edge substantially within said catheter body so as to draw material not substantially extending through the side opening cutting window into the catheter body.

19. The catheter of claim 18 wherein said cutting blade is scoop shaped.

20. The catheter of claim 18 wherein the cutting blade comprises a material collection surface that is located behind the the cutting blade edge to urge material removed from the body lumen towards the catheter body.

21. The catheter of claim 18 wherein the cutting blade moves along a path that is non-parallel with the longitudinal axis.

22. An atherectomy catheter comprising:

a catheter body comprising a proximal portion, a distal portion, a longitudinal axis, and an outer diameter;

a cutting window disposed on the distal portion of the catheter body;

a cutting element that is axially movable on a path that is non-parallel with the longitudinal axis of the catheter body, wherein the cutting element is movable from a first position in which the cutting element is within the catheter body to a second position in which the cutting element is out of the cutting window beyond the outer diameter of the catheter body; and a flexible elongated body for actuating the cutting element from the first position to the second position.

23. The catheter of claim 22 wherein the cutting element is rotatable.

24. The catheter of claim 22 wherein the distal portion of the catheter body can be urged into an angled orientation relative to the proximal portion of the catheter.

25. The catheter of claim 24 wherein the angled orientation can bias a section of the distal portion against a body lumen wall so as to position the cutting element adjacent a target tissue.

26. The catheter of claim 22 wherein the flexible elongated body comprises a pull-wire.

27. The catheter of claim 22 wherein the flexible elongated body comprises a driveshaft coupled to the cutting element.

28. The catheter of claim 22 wherein the distal portion of the catheter body comprises a ramp to direct the cutting element out of the cutting window.

* * * * *